(12) United States Patent
Hörth et al.

(10) Patent No.: US 7,383,969 B2
(45) Date of Patent: *Jun. 10, 2008

(54) DEVICE FOR MIXING AND DISPENSING MULTI-COMPONENT COMPOSITIONS

(75) Inventors: Hans Hörth, Hamburg (DE); Steffen Reuss, Hamburg (DE); Hans-Dieter Höhnk, Reinbek (DE)

(73) Assignee: Ernst Muhlbauer GmbH & Co. KG, Norderfriedrichskoog (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/543,497

(22) Filed: Oct. 5, 2006

(65) Prior Publication Data

US 2007/0023450 A1 Feb. 1, 2007

Related U.S. Application Data

(62) Division of application No. 10/718,393, filed on Nov. 20, 2003.

(30) Foreign Application Priority Data

Nov. 21, 2002 (DE) .............................. 102 54 409

(51) Int. Cl.
*B67D 5/60* (2006.01)
(52) U.S. Cl. .................. 222/145.6; 222/94; 222/145.5; 222/327; 222/491; 222/516; 222/548; 401/271; 401/281
(58) Field of Classification Search .................. 222/94, 222/145.5, 494, 145.6, 506, 212, 505, 516–518, 222/491, 495, 519, 548, 544, 549, 566–568, 222/327; 239/302–304, 402, 414–416; 401/270–271, 401/281
See application file for complete search history.

(56) References Cited

U.S. PATENT DOCUMENTS

| 3,200,995 | A | | 8/1965 | Gangwisch |
| 3,876,118 | A | | 4/1975 | Loredo |
| 4,771,919 | A | | 9/1988 | Ernst |
| 4,846,373 | A | | 7/1989 | Penn et al. |
| 5,152,432 | A | | 10/1992 | De Laforcade |
| 5,228,599 | A | | 7/1993 | Keller |
| 5,413,253 | A | * | 5/1995 | Simmen ...................... 222/137 |
| 5,443,183 | A | | 8/1995 | Jacobsen et al. |
| 6,135,631 | A | | 10/2000 | Keller |
| 6,352,177 | B1 | * | 3/2002 | Bublewitz et al. ............ 222/82 |
| 6,398,077 | B1 | | 6/2002 | Gross et al. |

FOREIGN PATENT DOCUMENTS

| DE | 25 28 116.7 | 6/1975 |
| DE | 295 18 531.7 | 11/1995 |
| EP | 0319 135 A2 | 10/1988 |

* cited by examiner

*Primary Examiner*—Frederick C. Nicolas
(74) *Attorney, Agent, or Firm*—Alix, Yale & Ristas, LLP

(57) ABSTRACT

A device for mixing and dispensing multi-component compositions employs a cap. The cap acts as a closure initially to close the outlet openings of the components and can be moved into the open position by pressure of the components while they are being discharged, so that the components can be mixed by the mixing helix and emerge from the outlet tube. The device also includes a distribution structure that may be a fitted onto or an integral part of the outlet tube.

18 Claims, 10 Drawing Sheets

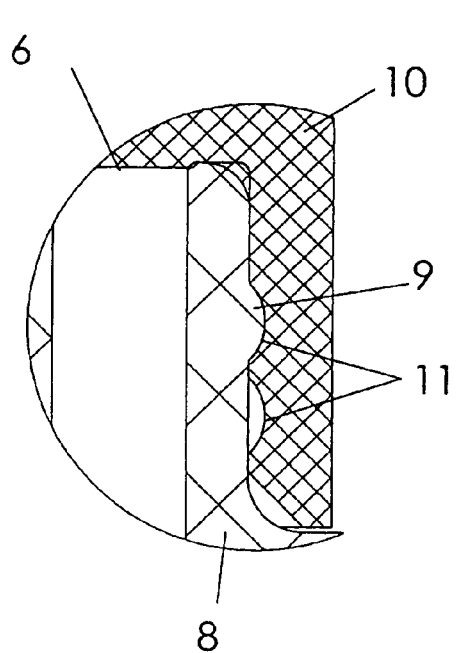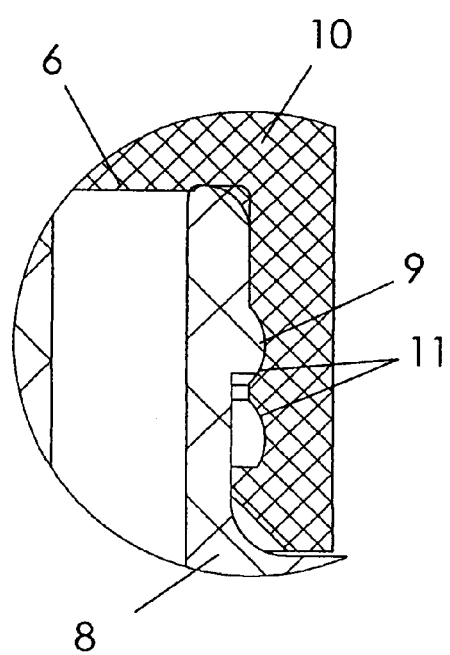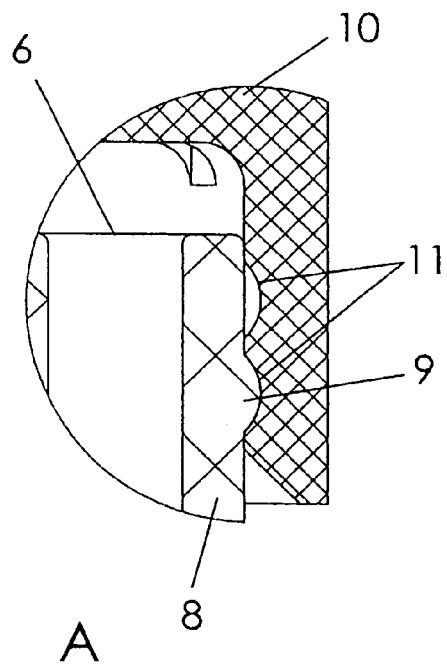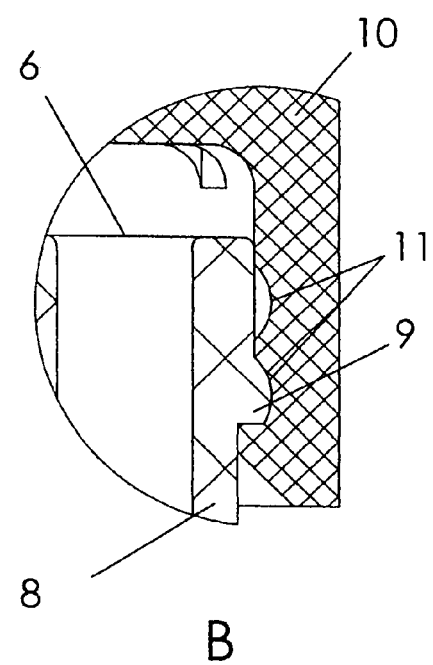
Fig.3      Fig.4

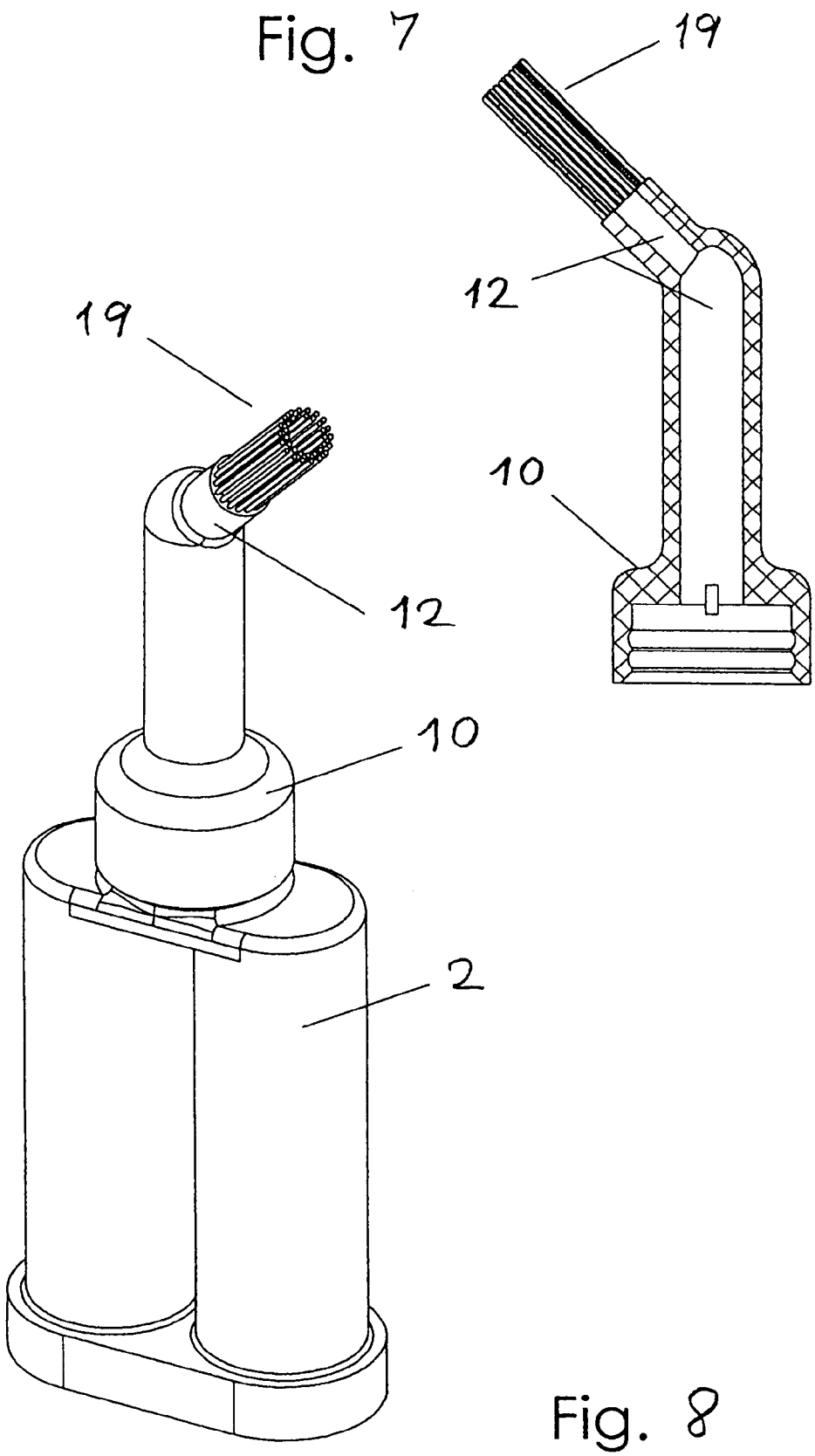

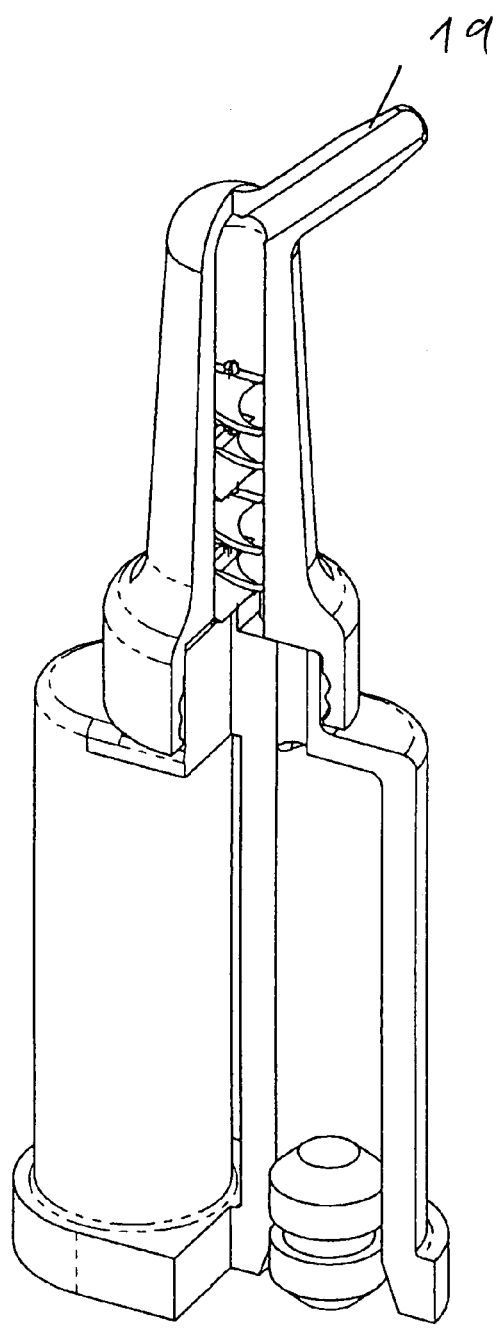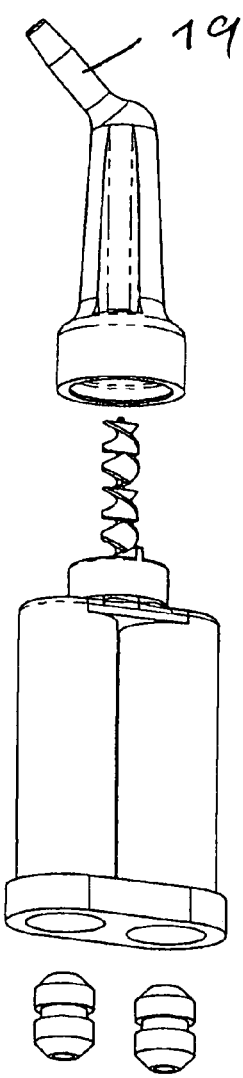
Fig. 19
Fig. 20

DEVICE FOR MIXING AND DISPENSING MULTI-COMPONENT COMPOSITIONS

CROSS REFERENCE TO RELATED APPLICATIONS

This application is a divisional of U.S. patent application Ser. No. 10/718,393, filed Nov. 20, 2003.

BACKGROUND OF THE INVENTION

The invention relates to a device for mixing and dispensing multi-component compositions, in particular for dental purposes, with a cartridge with at least two cylindrical chambers arranged in parallel for receiving the components and in each case a plunger for discharging the components, the chambers having outlet openings which are covered by a cap, which has an outlet tube enclosing a mixing helix, the cap being movable from a position closing the outlet openings into a position releasing them.

A known device of this type, which however is not intended for dental purposes (EP 0319 135 A2), has two cylindrical chambers, in each of which one component is contained. The chambers are provided on their end face with openings which are closed by a cap. The cap has a sleeve-shaped outlet tube, which encloses a mixing helix. The cap initially closes the openings of the chamber. If the two-component composition is to be dispensed, the cap is pulled, so that it moves away a little from the cartridge with the two chambers and releases the outlet openings. With the aid of plungers in the chambers, on which pressure is exerted, the components can then be pressed into the cap and from there into the sleeve-shaped outlet tube. While passing through this outlet tube, the components are mixed by the mixing helix.

Such devices are also very expedient for dental purposes. There is no need to provide a separate closure cap that has to be removed and replaced with a cap which contains the outlet tube and the mixing helix. However, a disadvantage of such devices is that a separate manipulation is required for pulling the cap to bring it into the open position. This is not only laborious; there is also the risk of inadvertently pulling the cap off entirely. Problems also arise in the production of such already known devices. As far as possible, the same model of the cartridges is intended to be supplied with different caps. Depending on the intended application, straight or curved outlet tubes are required. These caps must then also be respectively provided with a mixing helix, making them relatively expensive parts. Furthermore, the fitting of the mixing helix in the cap is not entirely simple.

The object of the invention is to provide a device of the type stated at the beginning which can be operated easily and unproblematically and allows low-cost and practical mass production.

SUMMARY OF THE INVENTION

The solution according to the invention comprises that the cap can be moved into the open position by the pressure of the components while they are being discharged and that a transverse wall which extends toward the cap and on which the mixing helix is fitted is provided on the cartridge between the outlet openings.

There is consequently no longer any need to pull the cap. Rather, it has an inner surface, opposite from the cartridge, which is large enough for the pressure of the components when they are being discharged to move the cap into the open position. The mixing helix is in this case fitted on the cartridge and not on the cap. For this purpose, it is fitted on a transverse wall, which has the further advantage that the two or more components cannot easily get into the chamber of the other component respectively during the dispensing operation, and for example cause hardening, and consequently make the device unable to operate.

The cap is expediently rotatable with respect to the cartridge, since, in the case of a curved outlet tube; the operator can then set this outlet tube in the way most expedient for him. However, the rotatability is only ensured when the cap has been moved into the open position. For this purpose, with the cap closed, the transverse wall is enclosed by the cap or is gripped by it on both sides in such a way that turning is not possible. As a result, it is possible to form the inner surface regions of the cap, which are intended to close the outlet openings of the chambers, optimally for this purpose.

If the mixing helix is flexible, caps with outlet tubes that have different curvatures can be used.

The device expediently has latching means for the closed and open positions. In this case, the latching means for the closed position must of course be adapted in its holding force to the opening force produced by the pressure of the components, in order that the cap can actually be opened just by pressure exertion and it does not have to be pulled.

The latching means for the open position expediently has a greater holding force than the latching means for the closed position, since otherwise there is the risk of the cap being detached completely from the cartridge if, after opening, the operator does not reduce the force which is required for opening. For this purpose, it may be provided that the latching means for the open position is a snap-action latching means, which provides a greater force of resistance opposing a further opening movement of the cap than a closing movement. For this purpose, surfaces which are for example sawtooth shaped in cross section may be provided, the sloping surfaces making it easier for the cap to be pushed onto the cartridge, but the surfaces perpendicular to the axis then preventing the cap from being detached when there is a movement in the opposite direction, that is for pulling off the cap.

Although the device may be designed for more than two components, it is designed particularly expediently for two components and correspondingly with two chambers. The device according to the invention is suitable in particular for once-only use. It can also be made to be relatively small and be actuated by a discharging device or, with the aid of an adapter, by means of a relatively large pair of grippers. The discharging device or the adapter may in this case be formed with surfaces which securely hold the cap, so that the latter cannot move any further after opening, become detached from the cartridge and get into the patient's mouth.

A means 19 for distributing or uniformly applying/introducing the multi-component composition is advantageously provided at the outlet end of the outlet tube 12. This means 19 may be a brush, a small sponge, a nozzle, a spatula or the like. The means 19 may be formed as an additional attachment which is attached onto the outlet tube 12. The means 19 may, however, also be formed in one piece with the outlet tube 12.

BRIEF DESCRIPTION OF THE DRAWINGS

The invention is described below by way of example on the basis of an advantageous embodiment with reference to the accompanying drawings, in which, in a perspective, partly cut-open view:

FIG. 3 shows detailed views in the section of the embodiment of FIGS. 1 and 2;

FIG. 4 shows detailed views of a slightly different embodiment;

FIG. 7 shows in section an outlet tube with a 10 means for distributing the finished multi-component composition;

FIG. 8 shows in a perspective view another embodiment with a means for distributing the finished multi-component composition; and FIGS. 9-20 show further views and embodiments.

DETAILED DESCRIPTION OF THE PREFERRED EMBODIMENTS

Figure 1:
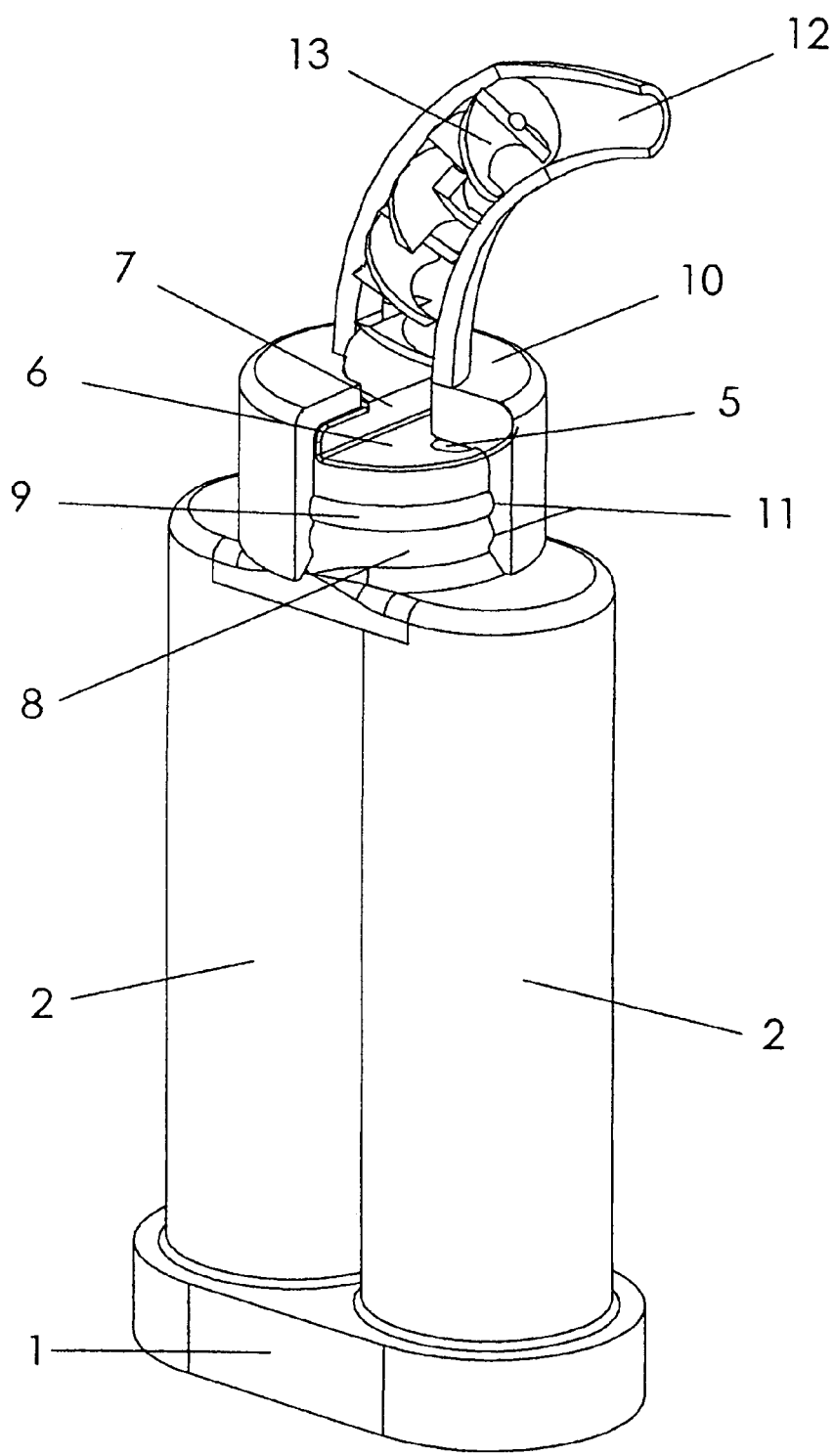
FIG. 1 shows the device in the closed state.
Figure 2:
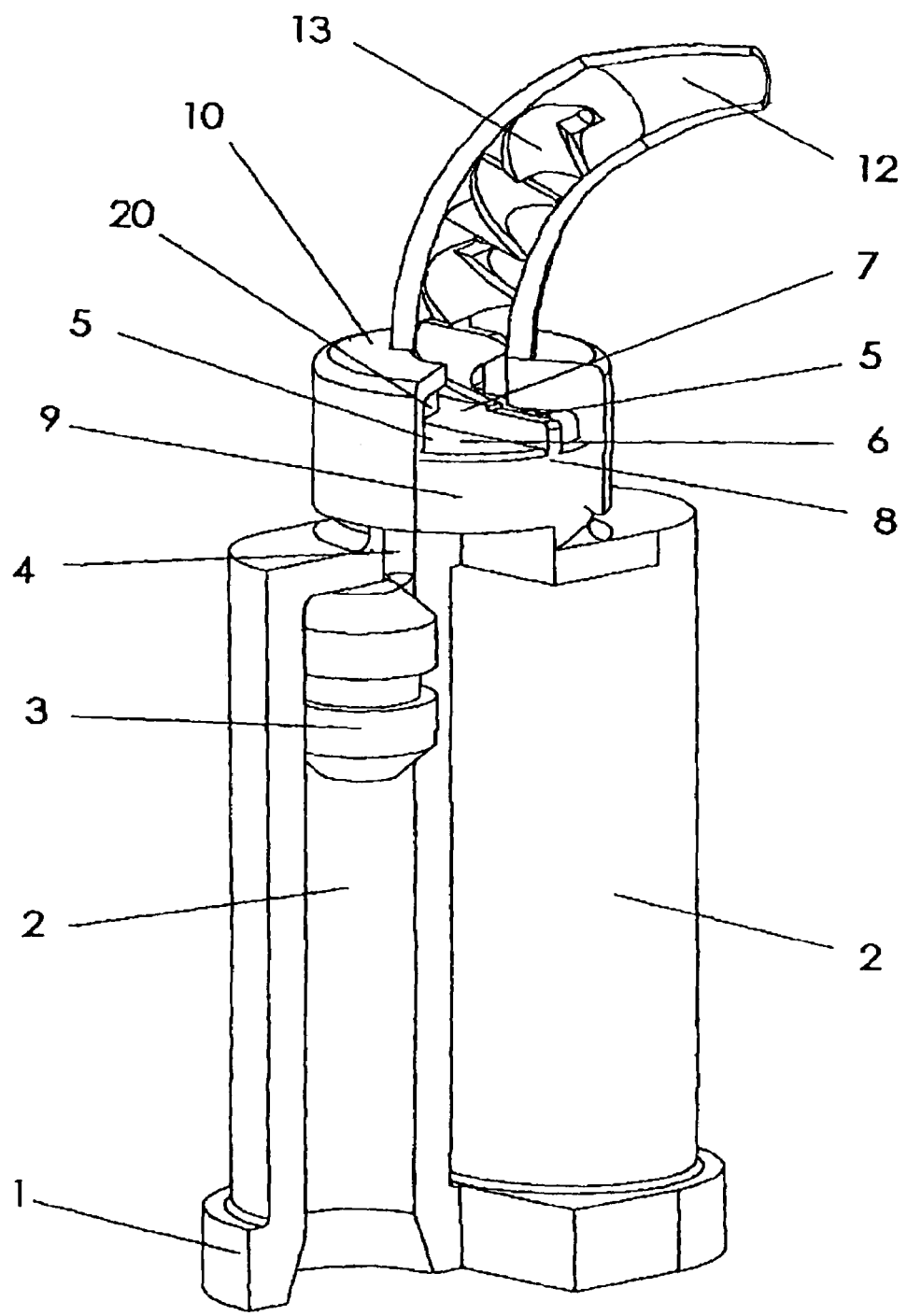
FIG. 2 shows the device, partly cut open, in the open state.

The device of the invention, which is shown in FIGS. 1 and 2, has a cartridge 1, which comprises two cylindrical chambers 2, arranged in each of which are a component (not shown) and a plunger 3 (FIG. 2), by which pressure can be exerted from the bottom (in the figures) upward by a suitable implement, in order to press the components upward through channels 4 and openings 5. These openings are provided on a circular surface 6, which is subdivided by a transverse wall 7. The surface 6 is in this case located on a circular-cylindrical projection of the cartridge which has an annular bead 9. Fitted on this cylindrical projection 8 is a cap 10, which has on its inner wall annular recesses 11, which interact with the annular bead 9. The cap 10 has a curved outlet tube 12, which encloses a mixing helix 13, which is fastened on the transverse wall 7. In the closed state, which is shown in FIG. 1, the annular bead 9 engages in the upper annular recess 11 of the cap 10. The substantially circular inner surface of the cap 10 in this case covers over the openings 5, so that the chambers 2 are closed. The transverse wall 7 is securely held against twisting in a recess 20, which can be seen in FIG. 2. If pressure is exerted on the plungers 3, and consequently the components, the cap is moved by this pressure from the position shown in FIG. 1 into the position shown in FIG. 2. The cylindrical inner surface of the cap 10 thereby moves away from the outlet openings 5, so that the components can emerge. The components are in this case separated from each other by the transverse wall 7, so that one component cannot readily get into the chamber 2 of the other component respectively. The transverse wall 7 is then no longer held by the recess 20, so that the cap 10 can be turned and the operator can turn the outlet tube 12 into the direction that is particularly expedient for him.

FIG. 3 shows detailed representations of how the cap 10 is securely held with the aid of the annular bead 9 and the recesses 11. At the top it is shown at A that the annular bead is located in the upper recess 11, that is to say, the cap 10 is assuming its lower position and closing the openings 5. In the case of the representation B, the cap has moved upward and is held in this open position at its lower recess 11 by the bead 9.

The embodiment of FIG. 4 differs from that of FIG. 3 in that the bead 9 of the cylindrical projection 8 of the cartridge has a lower straight surface, the lower recess 11 of the cap 10 likewise having a corresponding straight surface. The interaction of these straight surfaces prevents the cap 10 from being able to move further upward from the open position shown at B in FIG. 4. As a result, flipping off of the cap 10, for example into the patient's mouth, is prevented.

Figure 5:
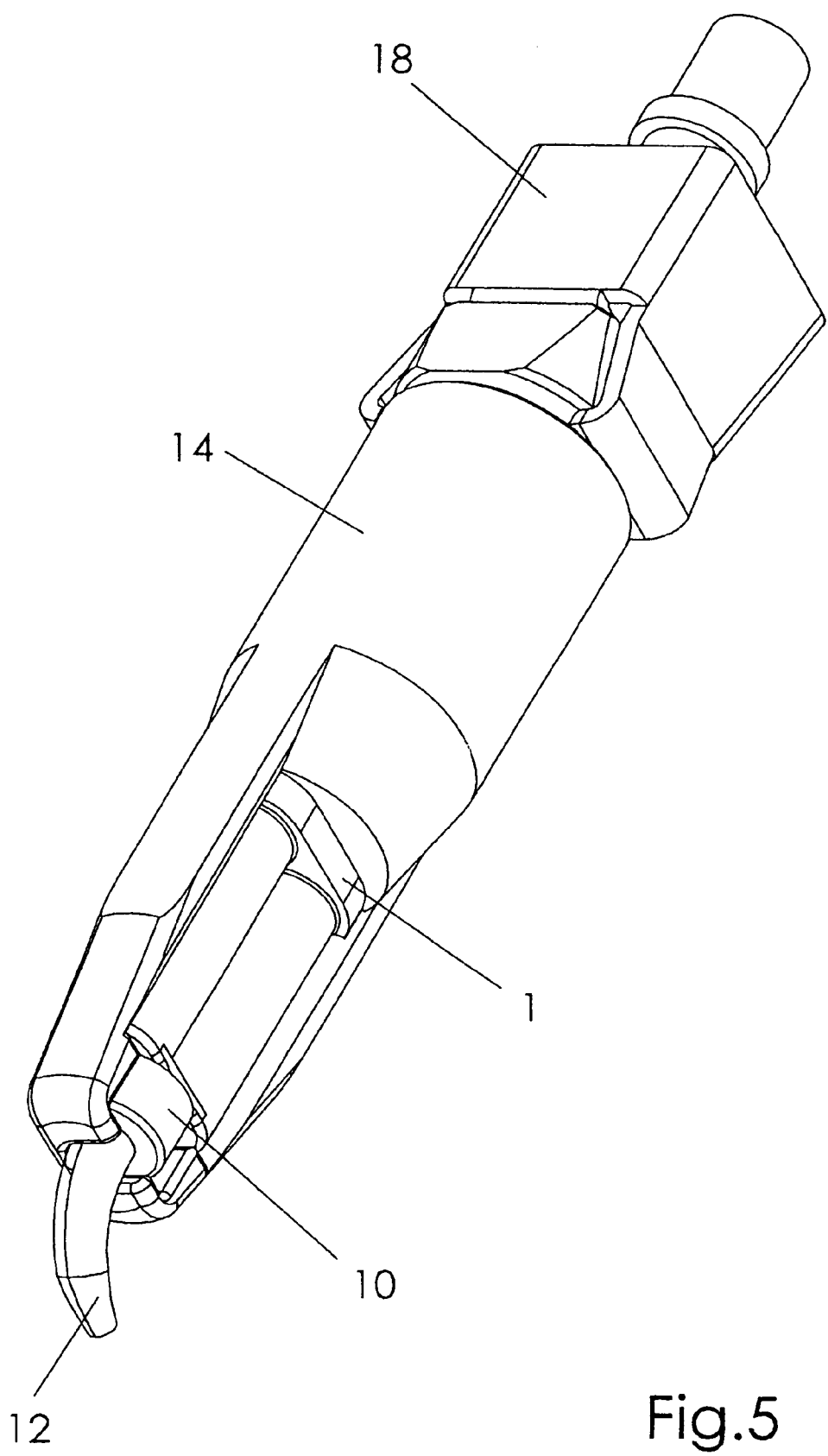
FIG. 5 shows the use of the device according to the invention in a pair of discharging grippers with an adapter.

Shown in FIG. 5 is an adapter 14, which has an upper opening into which the cartridge 1 with the cap 10 and the outlet tube 12 can be fitted. This adapter 14 may in turn be fitted onto a pair of grippers 18, which are intended for other, in particular larger cartridges, and are commercially available.

Figure 6:
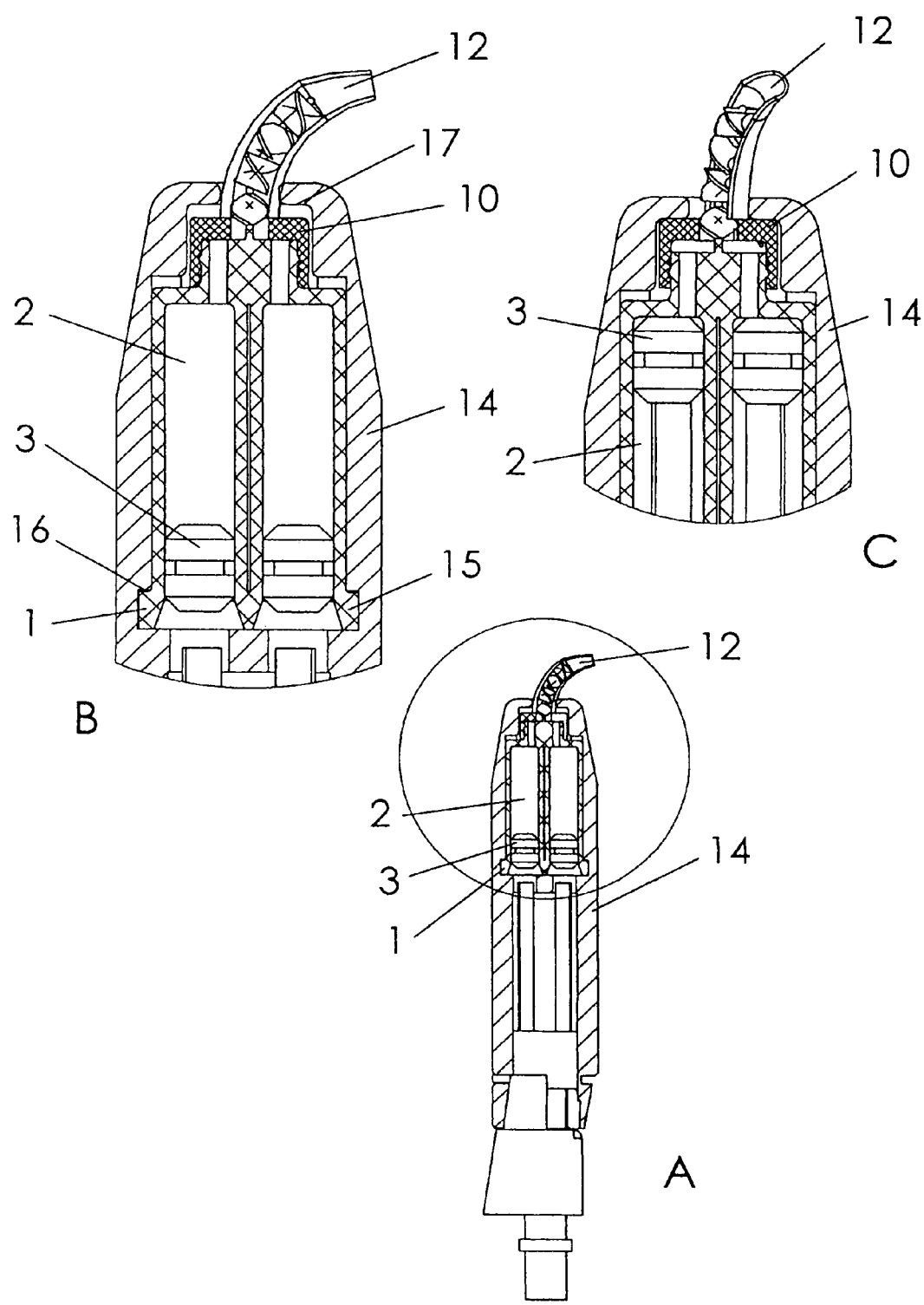
FIG. 6 shows details in section of the adapter of FIG. 5 with the device according to the invention fitted.
Figure 9:
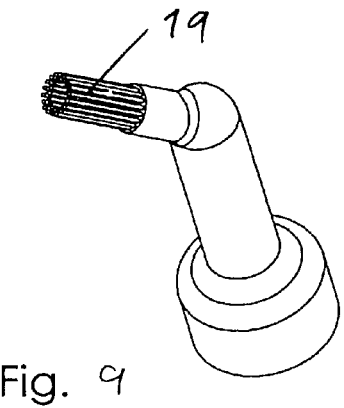

FIG. 6 shows in section the adapter 14 with the cartridge 1 fitted. An overall view is shown at A, detailed views are represented at B and C. In the case of the position of B in FIG. 6, the cartridge 1 is hindered from upward movement at its base part 15 by a stop face 16 when pressure is exerted on the plungers 3. A further stop face 17 prevents the cap 10 from any further upwardly directed movement when it moves from the closed position (at B in FIG. 6) into the open position (at C in FIG. 6). Consequently, this stop face 17 reliably prevents the cap 10 from being able to flip off. The adapter has in this case the advantage that the device according to the invention can also be used with other commercially available grippers. It goes without saying that this is not intended to exclude the possibility of also providing special grippers for the devices according to the invention, these grippers then also being covered by the extent of protection of this patent.

Figure 11:
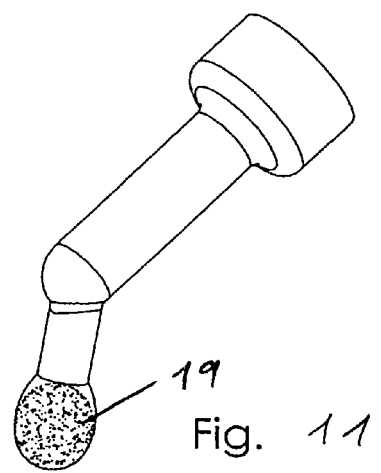
Figure 10:
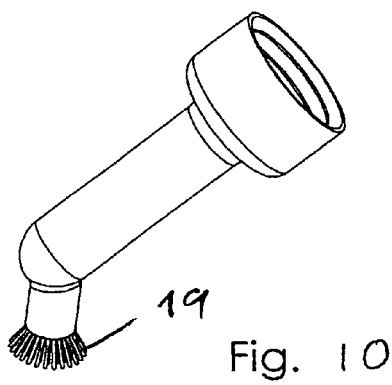
Figure 13:
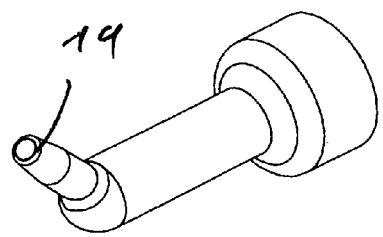
Figure 12:
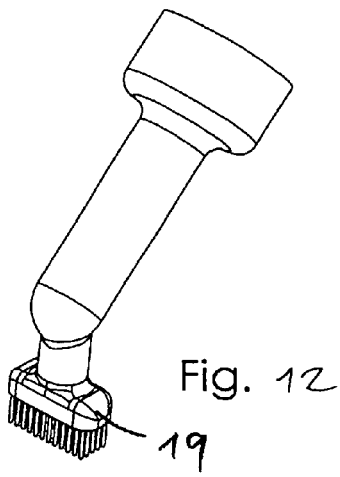
Figure 14:
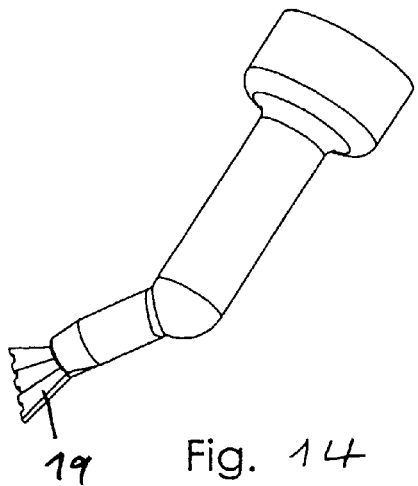

Shown in FIG. 7 is a cross section through another embodiment of the outlet tube 12, in which a device 19 is arranged at the outlet end of the same for distributing or spreading the discharged multi-component composition. The device 19 for distributing or spreading can be a brush (FIGS. 7, 8, 9, 10, 17, 18), a small sponge (FIG. 11), a brush (FIG. 12), a nozzle (FIGS. 13, 19, 20), a spatula (FIG. 14) or a similar device.

Figure 15:
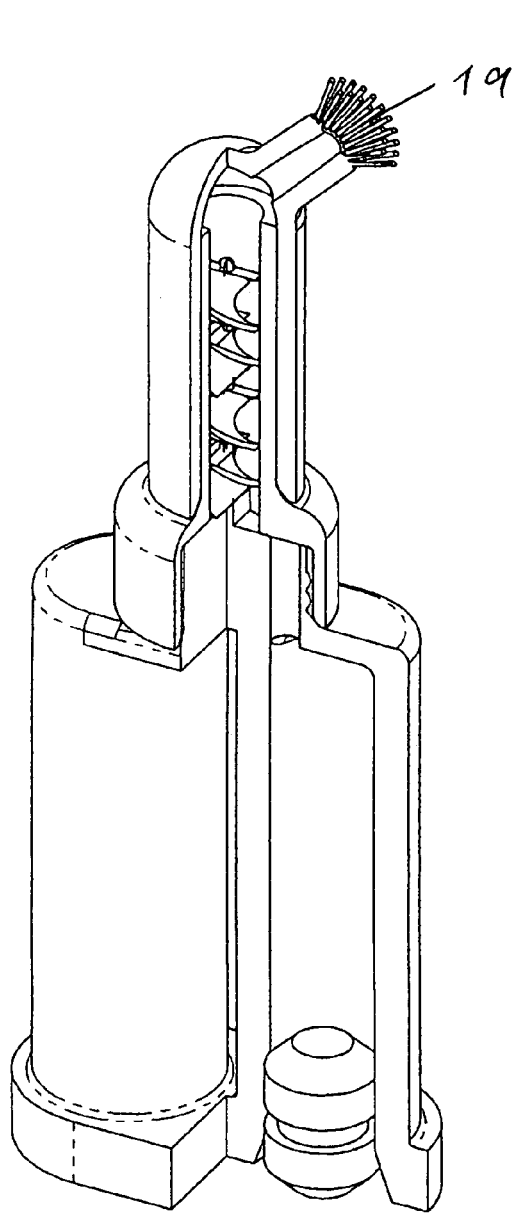
Figure 16:
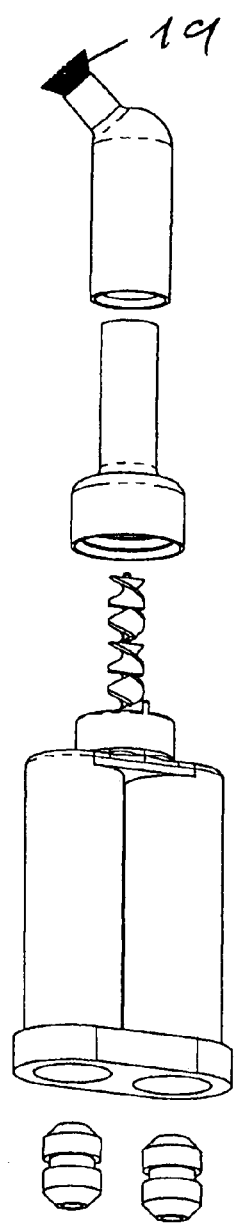
Figure 17:
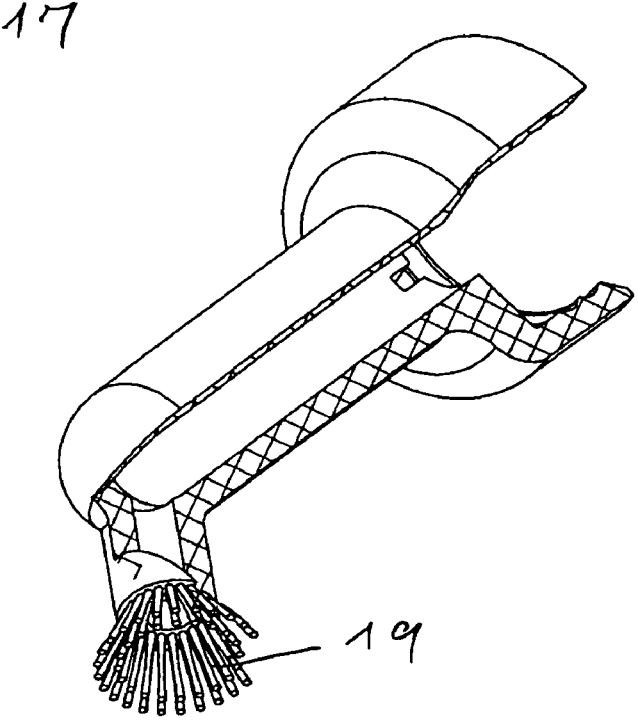
Figure 18:
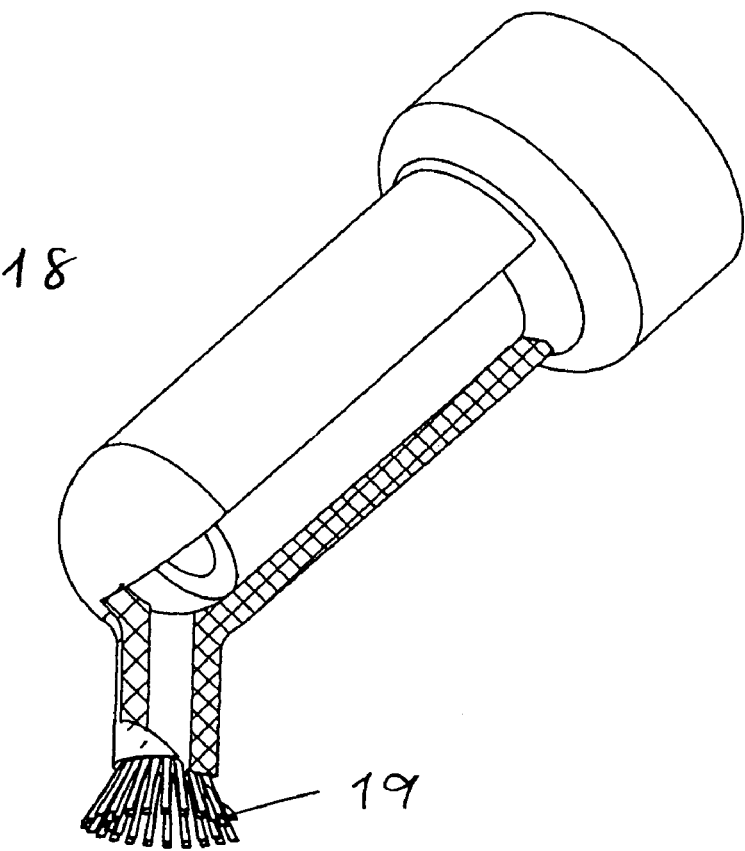

By contrast with the embodiment of FIG. 7, in the case of the embodiment of FIG. 8 the means 19 for distributing the finished multi-component composition onto the outlet tube 12 has been fitted, so that various parts 19 can optionally be fitted here on the outlet tube 12. This is shown also in the embodiment of FIGS. 15 and 16.

What is claimed:

1. A device for mixing and dispensing multi-component compositions of at least two components with a cartridge with at least two cylindrical chambers arranged in parallel for receiving the components and in each case a plunger for applying pressure to and discharging the components, the chambers having outlet openings which are covered by a cap, which has an outlet tube enclosing a mixing helix, the cap being movable from a closed position closing the outlet openings into an open position opening the outlet openings, wherein the cap is moved into the open position by the pressure of the components produced by the plunger while said components are being discharged in a discharging direction and a transverse wall which extends toward the cap is provided on the cartridge between the outlet openings, and a discharging device has a plurality of stop faces which restrict movement in the discharging direction, wherein said plurality of stop faces further comprises a first stop face for the cartridge and a second stop face for the cap in the open position.

2. The device as claimed in claim 1, comprising an adapter for use with grippers for other cartridges.

3. The device as claimed in claim 1, wherein the cap is rotatable with respect to the cartridge and in the closed position encloses the transverse wall in such a way that this turning movement is prevented.

4. The device as claimed in claim 1, wherein the mixing helix is flexible.

5. The device as claimed in claim 1, comprising latching means for the closed and open positions.

6. The device as claimed in claim 5, wherein the latching means for the open position has a greater holding force than the latching means for the closed position.

7. The device as claimed in claim 5, wherein the latching means for the open position is a snap-action latching means, which provides a greater force of resistance opposing a further opening movement of the cap than a closing movement.

8. The device as claimed in claim 1, wherein there are two chambers.

9. The device as claimed in claim 1, further comprising employing said device in dental applications.

10. A device for mixing and dispensing multi-component compositions of at least two components with a cartridge with at least two cylindrical chambers arranged in parallel for receiving the components and in each case a plunger for applying pressure to and discharging the components, the chambers having outlet openings which are covered by a cap, which has an outlet tube enclosing a mixing helix, the cap being movable from a closed position closing the outlet openings into an open position opening the outlet openings, wherein the cap is moved into the open position by the pressure of the components produced by the plunger while said components are being discharged and a transverse wall which extends toward the cap is provided on the cartridge between the outlet openings, and means for distributing the discharged multi-component composition.

11. The device as claimed in claim 10, wherein the means for distributing the discharged multi-component composition is formed in one piece with the outlet tube.

12. The device as claimed in claim 10, wherein the means for distributing the discharged multi-component composition is detachably fitted onto the outlet tube.

13. The device as claimed in claim 10, wherein the means for distributing the discharged multi-component composition is selected from the group consisting of a brush, a small sponge, a nozzle and a spatula.

14. The device as claimed in claim 10, wherein the mixing helix is flexible.

15. The device as claimed in claim 10, comprising latching means for the closed and open positions.

16. The device as claimed in claim 15, wherein the latching means for the open position is a snap-action latching means, which provides a greater force of resistance opposing a further opening movement of the cap than a closing movement.

17. The device as claimed in claim 10, wherein there are two chambers.

18. The device as claimed in claim 10, further comprising employing said device in dental applications.

\* \* \* \* \*